United States Patent [19]

Inatomi et al.

[11] Patent Number: 5,159,068
[45] Date of Patent: Oct. 27, 1992

[54] SEQUENCE OF DNA WHICH CODES MAIN SUBUNITS OF ATP SYNTHASE DERIVED FROM METHANOGENIC BACTERIA

[75] Inventors: Kenichi Inatomi, Amagasaki; Masamitsu Futai, Ibaraki, both of Japan

[73] Assignee: Mitsubishi Denki Kabushiki Kaisha, Tokyo, Japan

[21] Appl. No.: 527,940

[22] Filed: May 24, 1990

[30] Foreign Application Priority Data

Jun. 16, 1989 [JP] Japan .................. 1-154891

[51] Int. Cl.$^5$ ............................................. C12N 15/54
[52] U.S. Cl. ...................................................... 536/27
[58] Field of Search ............................................. 536/27

[56] References Cited

PUBLICATIONS

Methods in Molecular Biology, edited by John M. Walker (1984) pp. 213-219 and 242-259.
Discovering Enzymes, edited by David Dressler & Huntington Potter (1991) pp. 85 & 186.
Suggs et al., Proc. Natl. Acad. Sci. USA, vol. 78, #11, pp. 6613-6617, Nov. 1981.
Lehninger, Biochemistry, 1970, pp. 93-98.
Journal of Biological Chemistry, vol. 264, No. 19, Jul. 5, 1989, pp. 10954-10959, Ken-Ichi Inatomi et al., "Amino Acid Sequence of the $\alpha$ and $\beta$ Subunits of *Methanosarcina barkeri* ATPase Deduced from Cloned Genes".
Journal of Bacteriology, Dec. 1988, pp. 5960-5962, vol. 170, No. 12, Ken-Ichi Inatomi et al., "Isolation of Subunits from *Methanosarcina bakeri* ATPase: Nucleotide-Binding Site in the $\alpha$ Subunit".
Journal of Bacteriology, Sep. 1986, pp. 837-841, vol. 167, No. 3, Ken-Ichi Inatomi, "Characterization and Purification of the Membrane-Bound ATPase of the Archaebacterium *Methanosarcina barkeri*".

*Primary Examiner*—Richard A. Schwartz
*Assistant Examiner*—S. L. Nolan
*Attorney, Agent, or Firm*—Oblon, Spivak, McClelland, Maier & Neustadt

[57] ABSTRACT

A DNA sequence, characterized by coding the main subunits of the ATP synthase from methanogenic bacteria.

4 Claims, No Drawings

SEQUENCE OF DNA WHICH CODES MAIN SUBUNITS OF ATP SYNTHASE DERIVED FROM METHANOGENIC BACTERIA

BACKGROUND OF THE INVENTION

1. Field of the Invention

This invention relates to a sequence of DNA which codes the main subunits of ATP synthase (ATP ase) derived from methanogenic bacteria. The methanogenic bacteria, which have been reformed by plasmids having this DNA sequence, are capable of performing the effective synthesis of ATP (adenosine triphosphate), hence they are useful as the fixing microorganism for a high efficiency methane-fermenting bio-reactor, or in the environmental treatment such as sewage disposal, etc.

2. Discussion of Background

In connection with the ATP synthase, the sequence of DNA has so far been analyzed to the fullest extent in those microorganisms such as a colon bacillus (*Escherichia coli*), etc., or mitochondria of eukaryotic cells. However, since the methanogenic bacterium is absolutely aerophobic and difficult to grow under ordinary conditions, its biochemical characteristics are scarcely clarified. As the consequence, there has been no example of analysis of the DNA sequence in the ATP synthase relative to the methanogenic bacteria.

Accordingly, it has not been possible to utilize the enzymes for ATP synthesis which is important to grow the methanogenic bacteria, for their improvement.

The present inventors have so far been conducting researches and studies on the ATP synthase of methanogenic bacteria (vide: a thesis by K. Inatomi, published in "Journal of Bacteriology", Vol. 167, pp 837–841 (1986)), but the sequence of the enzyme has yet to be clarified.

As the results of diligent and strenuous efforts in their studies and researches, the present inventors have succeeded in obtaining plasmids containing therein the DNA sequence which codes the ATP synthase from the methanogenic bacteria, transforming the colon bacillus "*Escherichia coli*" with the thus obtained plasmids, isolating the plasmids from this colon bacillus "*Escherichia coli*" as transformed, and finally determining the sequence of DNA which codes the essential subunits of the ATP synthase contained in the thus isolated plasmids. As the result of this success, they have arrived at the present invention.

SUMMARY OF THE INVENTION

In view of the above-mentioned difficulty in determining the DNA sequence of the ATP synthase relative to the methanogenic bacteria, it is the principal object of the present invention to provide a DNA sequence which codes the main subunits of the ATP synthase from the methanogenic bacteria.

According to the present invention, in one aspect of it, there is provided a DNA sequence characterized by coding the main subunits of the ATP synthase derived from methanogenic bacteria.

According to the present invention, in another aspect of it, there is provided a DNA sequence, wherein the ATP are derived from "*Methanosarcina barkeri*".

According to the present invention in still another object of it, there is provided a DNA sequence, wherein, among the main subunits in the ATP synthase, α-subunit is shown to have the following amino acid sequence.

| 10 | 20 | 30 | 40 | 50 | 60 |
|---|---|---|---|---|---|
| MEVKGEIYRV | SGPVVTAIGL | QAKMYDLVKV | GNEGLMGEVI | QILGPKTIIQ | VYEETAGIKP |
| 70 | 80 | 90 | 100 | 110 | 120 |
| GEPCVSTGSS | LSVELGPGLL | SSIYDGVQRP | LHVLLEKMGS | FIQRGVSADG | LDHKKLWDFK |
| 130 | 140 | 150 | 160 | 170 | 180 |
| PIVKKGDSVK | GGDVIGVVQE | TVNIEHKIMV | PPDISGTISD | IKSGNFTVVD | TICTLTDGTE |
| 190 | 200 | 210 | 220 | 230 | 240 |
| LQMMQRWPVR | RPRPVKAKLT | PTRPLVTGMR | ILDGLFPVAK | GGTAAIPGPF | GSGKTVTQQS |
| 250 | 260 | 270 | 280 | 290 | 300 |
| LAKWSDTEIV | VYIGCGERGN | EMADVLSEFP | ELEDPQTGRP | LMERTVLIAN | TSNMPVAARE |
| 310 | 320 | 330 | 340 | 350 | 360 |
| ASVYTGITIA | EYYRDMGLDV | SLMADSTSRW | AEAMREISSR | LEEMPGEEGY | PAYLSARLAE |
| 370 | 380 | 390 | 400 | 410 | 420 |
| FYERAGVAES | LCGETGSITV | IGAVSPPGGD | FSEPVTQNTL | RIVKVFWALD | AKLSQRRHFP |
| 430 | 440 | 450 | 460 | 470 | 480 |
| AINWLNSYSL | YKDSLNDWFA | DNVAPDYVPL | RERAMEMLQT | ESELQEIVQL | VGSDALPDDQ |
| 490 | 500 | 510 | 520 | 530 | 540 |
| QLLLEITRML | REIFLQQNAF | HPVDAYSPFD | QQYKILKAIM | KWGDAAMDAL | KSGVPVTEII |
| 550 | 560 | 570 | 580 | | |
| KLESKNVLAK | VKYEEKFDES | MNAVLAQMDK | EFASLRGR | | |

According to the present invention, in other aspect of it, there is provided DNA sequences, wherein, among the main subunits in the ATP synthase, β-subunit is shown to have the following amino acid sequence.

| 10 | 20 | 30 | 40 | 50 | 60 |
|---|---|---|---|---|---|
| VKEYKTITQI | AGPLVFVEKT | EPVGYKEIVT | INLPDGTTRR | GEVLDSSSDI | VVIQIFEGTT |
| 70 | 80 | 90 | 100 | 110 | 120 |
| GLDKECGVVF | TGETLKLPAS | IDLLGRILSG | SGEPLDGGPR | IVPDQLLDIN | GAAMNPYARL |
| 130 | 140 | 150 | 160 | 170 | 180 |
| PPKDFIQTGI | STIDGTNTLV | RGQKLPIFSA | SGLPHNEIAL | QIARQAAVPG | SESAFAVVFA |
| 190 | 200 | 210 | 220 | 230 | 240 |
| AMGITNEEAQ | YFMSDFEKTG | ALERAVVFLN | LADDPAVERI | VTPRMALTAA | EYLAYEHGMH |
| 250 | 260 | 270 | 280 | 290 | 300 |
| VLVILTDITN | YAEALRQMGA | ARNEIPGRRG | YPGYMYTDLA | TLYERAGIVK | GAKGSVTQIP |
| 310 | 320 | 330 | 340 | 350 | 360 |

-continued

| | | | | | |
|---|---|---|---|---|---|
| ILSMPGDDIT | HPIPDLSGYI | TEGQIVVSRE | LHRKGIYPPI | NVLPSLSRLM | NSGIGAGKTR |
| 370 | 380 | 390 | 400 | 410 | 420 |
| EDHKAVSDQM | YAGYAEGRDL | RGLVAIVGKE | ALSERDVKFL | EFADLFEQQF | VTQGRNENRT |
| 430 | 440 | 450 | 460 | | |
| IADTLDIGWK | ILAHLPENQL | GRIDNKYIQK | YHPAHRKCQ | | |

According to the present invention in still other aspect of it, there is provided DNA sequences as shown below, which codes both α- and β-subunits, both being the main subunits of the ATP synthase.

| 10 | 20 | 30 | 40 | 50 | 60 |
|---|---|---|---|---|---|
| GCCGGAAATT | CTAAGGAAAA | ACTTGAATGA | GTCTGTCCAG | CCTACAGTAG | TAGCCCTGGG |
| 70 | 80 | 90 | 100 | 110 | 120 |
| AGGCAGTGGA | TCAGGCTCAA | ATCTAAGAGA | TAAGATAAAA | CAAGCGGTAG | GTGTTGATCT |
| 130 | 140 | 150 | 160 | 170 | 180 |
| GTGGAAGTAA | AAGGTGAAAT | TTATCGTCGC | TCTGGGCCTG | TCGTCACCGC | CATCGGCTTG |
| 190 | 200 | 210 | 220 | 230 | 240 |
| CAGGCAAAAA | TGTATGACCT | GGTCAAAGTC | GGTAATGAAG | GTTTAATGGG | TGAAGTCATT |
| 250 | 260 | 270 | 280 | 290 | 300 |
| CAGATATTAG | GGCCCAAGAC | CATCATCCAG | GTATATGAAG | AGACCGCAGG | TATCAAGCCA |
| 310 | 320 | 330 | 340 | 350 | 360 |
| GGGGAACCCT | GTGTATCTAC | AGGGTCGTCT | CTGTCCGTAG | AACTTGGTCC | GGGTCTTCTT |
| 370 | 380 | 390 | 400 | 410 | 420 |
| TCCAGTATTT | ATGACGGGGT | TCAAAGGCCT | CTGCACGTCC | TGCTTGAAAA | AATGGGTAGC |
| 430 | 440 | 450 | 460 | 470 | 480 |
| TTCATCCAGA | GAGGTGTCAG | CGCAGATGGG | CTTGATCATA | AGAAACTCTG | GGATTTCAAA |
| 490 | 500 | 510 | 520 | 530 | 540 |
| CCCATTGTCA | AGAAGGGCGA | TTCCGTAAAA | GGTGAGACG | TAATTGGTGT | TGTACAGGAA |
| 550 | 560 | 570 | 580 | 590 | 600 |
| ACCGTGAATA | TTGAACATAA | GATCATGGTG | CCTCCTGATA | TCTCAGGTAC | AATTTCCGAC |
| 610 | 620 | 630 | 640 | 650 | 660 |
| ATAAAGAGCG | GAAACTTTAC | GGTAGTAGAC | ACAATCTGTA | CTCTGACTGA | TGGGACCGAA |
| 670 | 680 | 690 | 700 | 710 | 720 |
| TTGCAGATGA | TGCAGAGGTG | GCCTGTTCGA | AGACCCAGAC | CTGTGAAGGC | AAAACTTACT |
| 730 | 740 | 750 | 760 | 770 | 780 |
| CCAACCAGGC | CTCTGGTTAC | AGGAATGAGA | ATCCTTGATG | GGCTTTTCCC | TGTGGCAAAA |
| 790 | 800 | 810 | 820 | 830 | 840 |
| GGCGGAACAG | CTGCAATCCC | CGGACCTTTC | GGATCGGGAA | AGACCGTAAC | TCAGCAGTCG |
| 850 | 860 | 870 | 880 | 890 | 900 |
| CTTGCAAAAT | GGAGTGATAC | CGAAATTGTG | GTCTACATCG | GTTGTGGTGA | GCGTGGAAAC |
| 910 | 920 | 930 | 940 | 950 | 960 |
| GAAATGGCAG | ATGTTCTGAG | CGAATTCCCT | GAACTCGAAG | ATCCGCAGAC | CGGGCGCCCA |
| 970 | 980 | 990 | 1000 | 1010 | 1020 |
| CTTATGGAGC | GTACTGTTCT | TATCGCTAAC | ACTTCAAACA | TGCCTGTGGC | CGCAAGAGAA |
| 1030 | 1040 | 1050 | 1060 | 1070 | 1080 |
| GCATCTGTGT | ATACCGGAAT | CACCATTGCA | GAATACTACC | GTGACATGGG | ATTAGATGTA |
| 1090 | 1100 | 1110 | 1120 | 1130 | 1140 |
| TCCCTTATGG | CAGACTCCAC | CTCAAGGTGG | GCAGAAGCCA | TGAGAGAAAT | CTCTTCCCGT |
| 1150 | 1160 | 1170 | 1180 | 1190 | 1200 |
| CTGGAAGAAA | TGCCTGGTGA | AGAAGGTTAC | CCAGCATACC | TGTCTGCAAG | ACTGGCCGAA |
| 1210 | 1220 | 1230 | 1240 | 1250 | 1260 |
| TTCTACGAGC | GTGCCGGGGT | TGCGGAGAGT | CTTTGCGGCG | AAACAGGTTC | CATTACTGTT |
| 1270 | 1280 | 1290 | 1300 | 1310 | 1320 |
| ATTGGAGCAG | TATCTCCACC | TGGCGGTGAC | TTCTCAGAGC | CTGTTACACA | GAATACCCTG |
| 1330 | 1340 | 1350 | 1360 | 1370 | 1380 |
| CGTATCGTAA | AAGTGTTCTG | GGCTCTCGAT | GCCAAACTAT | CTCAGAGGCG | TCACTTCCCG |
| 1390 | 1400 | 1410 | 1420 | 1430 | 1440 |
| GCCATCAACT | GGCTGAACAG | TTACAGTCTG | TATAAGGACA | GTCTTAATGA | CTGGTTTGCA |
| 1450 | 1460 | 1470 | 1480 | 1490 | 1500 |
| GATAATGTGG | CTCCTGATTA | TGTGCCTTTG | AGGGAAAGAG | CAATGGAAAT | GCTCCAGACA |
| 1510 | 1520 | 1530 | 1540 | 1550 | 1560 |
| GAATCTGAAC | TGCAGGAAAT | CGTGCAGCTT | GTAGGTTCCG | ATGCTCTGCC | AGACGACCAG |
| 1570 | 1580 | 1590 | 1600 | 1610 | 1620 |
| CAGCTTCTGC | TTGAAATCAC | CCGTATGCTT | AGGGAAATTT | TCCTGCAGCA | GAATGCATTC |
| 1630 | 1640 | 1650 | 1660 | 1670 | 1680 |
| CACCCAGTAG | ATGCATACAG | CCCGTTCGAT | CAGCAGTACA | AGATCCTTAA | GGCAATCATG |
| 1690 | 1700 | 1710 | 1720 | 1730 | 1740 |
| AAATGGGGAG | ACGCTGCGAT | GGATGCCTTG | AAATCAGGTG | TTCCCGTAAC | TGAAATTATC |
| 1750 | 1760 | 1770 | 1780 | 1790 | 1800 |
| AAGCTTGAAT | CCAAAAATGT | GCTTGCTAAG | GTCAAGTACG | AAGAGAAGTT | TGATGAGTCT |
| 1810 | 1820 | 1830 | 1840 | 1850 | 1860 |
| ATGAATGCTG | TCCTGGCACA | GATGGATAAA | GAGTTTGCAT | CCCTGAGAGG | TAGGTAAATA |
| 1870 | 1880 | 1890 | 1900 | 1910 | 1920 |
| TGGTAAAAGA | GTATAAGACA | ATCACTCAGA | TTGCAGGACC | ACTTGTCTTT | GTTGAAAAAA |
| 1930 | 1940 | 1950 | 1960 | 1970 | 1980 |
| CAGAGCCTGT | AGGCTATAAA | GAAATTGTTA | CTATTAACTT | GCCTGACGGG | ACCACCCGCA |
| 1990 | 2000 | 2010 | 2020 | 2030 | 2040 |
| GAGGCGAGGT | GCTGGACTCA | TCTTCAGACA | TAGTGGTTAT | CCAGATTTTT | GAAGGTACTA |

-continued

| | | | | | |
|---|---|---|---|---|---|
| 2050 | 2060 | 2070 | 2080 | 2090 | 2100 |
| CTGGTCTGGA | CAAGGAATCG | GGTGTAGTCT | TTACAGGGGA | AACCCTGAAG | CTCCCTGCAT |
| 2110 | 2120 | 2130 | 2140 | 2150 | 2160 |
| CCATTGACCT | TCTCGGAAGA | ATCCTTTCAG | GTTCAGGAGA | ACCACTTGAC | GGTGGACCCA |
| 2170 | 2180 | 2190 | 2200 | 2210 | 2220 |
| GGATTGTGCC | CGACCAGCTT | CTGGACATCA | ACGGAGCTGC | AATGAACCCA | TATGCCAGGC |
| 2230 | 2240 | 2250 | 2260 | 2270 | 2280 |
| TGCCTCCAAA | GGATTTCATC | CAGACAGGTA | TCTCCACAAT | AGACGGAACA | AATACCCTTG |
| 2290 | 2300 | 2310 | 2320 | 2330 | 2340 |
| TCCGTGGACA | GAAACTGCCT | ATTTTCTCAG | CTTCAGGTCT | TCCACACAAC | GAAATTGCTC |
| 2350 | 2360 | 2370 | 2380 | 2390 | 2400 |
| TGCAGATCGC | AAGGCAGGCT | GCTGTGCCAG | GATCTGAATC | TGCTTTCGCA | GTAGTTTTTG |
| 2410 | 2420 | 2430 | 2440 | 2450 | 2460 |
| CAGCAATGGG | TATTACCAAT | GAAGAAGCCC | AGTACTTCAT | GAGCGACTTC | GAAAAGACCG |
| 2470 | 2480 | 2490 | 2500 | 2510 | 2520 |
| GGGCTCTTGA | AAGGGCTGTT | GTGTTCCTCA | ACCTTGCAGA | TGACCCTGCT | GTCAACGTA |
| 2530 | 2540 | 2550 | 2560 | 2570 | 2580 |
| TAGTTACTCC | GCGTATGGCT | TTAACTGCAG | CTGAATATCT | GGCATACGAA | CACGGCATGC |
| 2590 | 2600 | 2610 | 2620 | 2630 | 2640 |
| ACGTACTTGT | CATTCTGACC | GACATTACCA | ACTATGCAGA | AGCTCTTCGT | CAGATGGGTG |
| 2650 | 2660 | 2670 | 2680 | 2690 | 2700 |
| CCGCTCGTAA | CGAAATCCCT | GGCCGTCGTG | GGTATCCTGG | TTACATGTAC | ACTGACCTTG |
| 2710 | 2720 | 2730 | 2740 | 2750 | 2760 |
| CAACTCTCTA | TGAGCGCGCA | GGTATTGTTA | AGGGCGCAAA | GGGATCAGTT | ACTCAGATTC |
| 2770 | 2780 | 2790 | 2800 | 2810 | 2820 |
| CGATTCTCTC | GATGCCTGGT | GACGATATTA | CCCACCCGAT | TCCTGACCTG | TCCGGTTATA |
| 2830 | 2840 | 2850 | 2860 | 2870 | 2880 |
| TTACTGAAGG | GCAGATTGTG | GTTTCAAGAG | AACTGCACAG | GAAAGGTATC | TACCCGCCAA |
| 2890 | 2900 | 2910 | 2920 | 2930 | 2940 |
| TTAATGTGTT | GCCGTCCCTG | TCAAGGTTGA | TGAACTCCGG | TATCGGACGA | GGCAAGACAA |
| 2950 | 2960 | 2970 | 2980 | 2990 | 3000 |
| GAGAAGACCA | CAAGGCAGTT | TCTGACCAGA | TGTATGCAGG | TTATGCAGAA | GGGCGTGACC |
| 3010 | 3020 | 3030 | 3040 | 3050 | 3060 |
| TGAGAGGTCT | CGTGGCTATC | GTCGGTAAAG | AAGCTCTGTC | TGAGAGAGAC | GTCAAGTTCC |
| 3070 | 3080 | 3090 | 3100 | 3110 | 3120 |
| TTGAGTTTGC | TGACCTTTTC | GAACAGCAGT | TCGTTACACA | GGGCAGAAAC | GAAAACAGGA |
| 3130 | 3140 | 3150 | 3160 | 3170 | 3180 |
| CAATTGCAGA | CACTCTGGAC | ATTGGATGGA | AGATCCTTGC | ACACCTGCCT | GAAAACCAGC |
| 3190 | 3200 | 3210 | 3220 | 3230 | 3240 |
| TGGGTAGGAT | TGACAACAAA | TACATCCAGA | AATACCATCC | TGCACACAGA | AAGGGTCAGT |
| 3250 | 3260 | 3270 | 3280 | 3290 | 3300 |
| GATTACCATG | GCTCAAGACG | TAAAACCAAC | TCGGTCGGAG | CTGATTGAGC | TCAAGAAAAA |
| 3310 | 3320 | 3330 | 3340 | 3350 | 3360 |
| AATCAAGCTC | TCTGAAAGTG | GGCACAAGCT | CCTTAAGATG | AAGAGAGATG | GTCTTATTCT |

The foregoing objects, other objects as well as specific way of determining the DNA sequence, etc. according to the present invention will become more apparent and understandable from the following detailed description of the invention to be made with reference to specific examples thereof.

DETAILED DESCRIPTION OF PREFERRED EMBODIMENT

The DNA sequence which codes the main subunits of the ATP synthesis from the methanogenic bacteria according to the present invention can be determined by the following method:

1) Methanogen is cultured, and then the cells are harvested, followed by isolation of chromosomal DNA; by the way, Methanogens are available from German Collection of Microorganism (DSM), Goettingen, West Germany;

2) this chromosomal DNA is digested with a restriction enzyme, and then plasmids, which play a role of vector, are digested with a restriction enzyme, followed by combining the thus obtained fragments of the chromosomal DNA and the digested plasmids with use of ligase; then, using this recombinant DNA plasmid as joined, those bacteria such as "*Escherichia coli*", etc., which can become the host, are subjected to transformation, with which a gene bank of the methanogenic bacterium is prepared;

3) as a method of selecting, from those strains, into which the recombinant DNA has been migrated, the transformed cells with the recombinant DNA to code the ATP synthase having been introduced into it, there may be employed a colony hybridization method, in which oligonucleotide labeled with $^{32}P$ is used as a probe;

4) the oligo-nucleotide to be used as the probe is synthesized on the basis of partial amino acid sequences containing therein amino-terminus sequences, resulted from purified α- and β-subunits as the main subunits from the ATP synthase which are purified from the methanogenic bacterium, and then determining the amino acid sequence in these subunits by means of a protein sequencer; and 5) the sequence of DNA to code the ATP synthesis is determined by the Sanger's di-deoxy method (vide: "Science", Vol. 214, page 1205 (1981)), or other methods.

By comparison of the amino acid sequence deduced from the thus DNA sequence with the amino acid sequences determined by the protein-sequencer, the DNA can be identified to code the main subunits of the enzyme.

As the hosts to be used for cloning in the present invention, there may be exemplified those bacteria belonging to the genus Escherichia. As the plasmids which play a role of the vector, there may be exemplified pUC 18, pUC 19, pBR 322, and so on.

With a view to enabling those persons skilled in the art to put the present invention into practice, the following preferred examples are presented. It should, however, be noted that these examples are illustrative only and not so restrictive, and that any changes and modifications may be made by those persons skilled in the art within the ambit of the present invention as recited in the appended claims.

EXAMPLE 1

Preparation of recombined DNA carrying therein genes which code main subunits of ATP synthase from methanogenic bacteria

*Methanosarcina barkeri* (Deposit No. DSM 800) was cultured in 1 liter of the medium of the following composition and about 1/100 (by volume) of the bacteria was inoculated. After two weeks at a temperature of 37° C., 6.0 g of the cells were obtained.

| | |
|---|---|
| $K_2HPO_4$ | 0.348 g |
| $KH_2PO_4$ | 0.227 g |
| $NH_4Cl$ | 0.5 g |
| $MgSO_4.7H_2O$ | 0.5 g |
| $CaCl_2.2H_2O$ | 0.25 g |
| NaCl | 2.25 g |
| $FeSO_4.7H_2O$ | 0.002 g |
| Vitamin solution | 10.0 ml |
| Solution of element in a tracing quantity | 3.0 ml |
| Yeast extract (product of Defico Co.) | 2.0 g |
| "Casitone" (product of Defico Co.) | 2.0 g |
| "Resazurian" | 0.001 g |
| $NaHCO_3$ | 0.85 g |
| $CH_3OH$ | 10.0 ml |
| Cysteine chloride | 0.3 g |
| $Na_2S.9H_2O$ | 0.3 g |
| Distilled water | appropriate quantity |
| TOTAL QUANTITY | 1,000.0 ml |

From the thus obtained cells, DNA was prepared by the Saito-Miura method as described in "Biochem. Biophys. Acta", Vol. 72, page 619 (1963), with the exception that the lysozyme treatment was carried out instead of SDS. This DNA was digested with a restriction enzyme of Sau 3A to obtain DNA fragments with 2-3 kb. Further, plasmid "pUC 18" was digested with a restriction enzyme of Bam Hl, and then it was ligated with the above-mentioned DNA fragment which was digested by the restriction enzyme Sau 3A overnight at a temperature of 13° C. with T4 ligase. Using this reaction mixture, *Escherichia coli* C-600 was transformed by the Mandel-Higa method as described in "Journal of Molecular Biology", Vol. 53, page 159 (1970).

EXAMPLE 2

Selection of recombinant DNA containing genes coding ATP synthase

*Escherichia coli* as transformed was grown on agar plates containing anpiciline (50 μg/ml), and then about 10,000 colonies which had grown was fixed on nitrocellulose. The highly purified α- and β-subunits were obtained by the method developed by K. Inatomi and M. Maeda (vide: "Journal of Bacteriology", Vol. 170, pp 5960 to 5962 (1988)). The amino terminus sequences of these subunits were determined with a protein sequencer to prepare DNA probes which correspond to their amino acid sequences. Table 1 below shows the DNA sequences of such synthesized DNA.

TABLE 1

| | α-subunit | | | | | | β-subunit | | | | | |
|---|---|---|---|---|---|---|---|---|---|---|---|---|
| Amino acid sequence | M E V K G Q(E) | | | | | | K E Y K T I | | | | | |
| DNA sequence | ATG | GAA GAG | GTT GTC GTA GTG | AAA AAG | GGT GGC GGA GGG | C(G)A C(G)A | AAA AAG | GAA GAG | TAT TAC | AAA AAG | ACT ACC ACA ACG | AT AT |

The thus obtained synthesized DNA was labeled with $^{32}P$, which was then subjected to hybridization with the above-mentioned colony on the nitro cellulose filter. From the results of this hybridization, there were selected three types of colonies which could be hybridized stably at 30° C.

Of these three types of strains as selected, there were selected, by use of the Southern's method (vide: "Journal of Molecular Biology", Vol. 98, page 503 (1975)), those strains which could hybridize with either synthesized probes of the α- and β-subunits. The recombinant DNA which this *Escherichia coli* carried was named "pMB-1".

EXAMPLE 3

Determination of DNA sequence and amino acid sequence of genes which code main subunits of ATP synthase from methanogenic bacteria In view of the fact that pMB-1 contained the gene coding the main subunits of the ATP synthase from the methanogenic bacteria, which is ligated to the plasmid pUC 18, it was determined by use of the di-deoxy method as described in the Sanger's literature (vide: "Science", Vol. 214, page 2105 (1981)). As the result, the DNA sequence, which codes the main subunits of the ATP synthase out of the total DNA sequences as determined, was as shown below.

| 10 | 20 | 30 | 40 | 50 | 60 |
|---|---|---|---|---|---|
| GCCGGAAATT | CTAAGGAAAA | ACTTGAATGA | GTCTGTCCAG | CCTACAGTAG | TAGCCCTGGG |
| 70 | 80 | 90 | 100 | 110 | 120 |
| AGGCAGTGGA | TCAGGCTCAA | ATCTAAGAGA | TAAGATAAAA | CAAGCGGTAG | GTGTTGATCT |
| 130 | 140 | 150 | 160 | 170 | 180 |
| GTGGAAGTAA | AAGGTGAAAT | TTATCGTGTG | TCTGGGCCTG | TCGTCACCGC | CATCGGCTTG |
| 190 | 200 | 210 | 220 | 230 | 240 |
| CAGGCAAAAA | TGTATGACCT | GGTCAAAGTC | GGTAATGAAG | GTTTAATGGG | TGAAGTCATT |
| 250 | 260 | 270 | 280 | 290 | 300 |
| CAGATATTAG | GGCCCAAGAC | CATCATCCAG | GTATATGAAG | AGACCGCAGG | TATCAAGCCA |
| 310 | 320 | 330 | 340 | 350 | 360 |
| GGGGAACCCT | GTGTATCTAC | AGGGTCGTCT | CTGTCCGTAG | AACTTGGTCC | GGGTCTTCTT |

| 370 | 380 | 390 | 400 | 410 | 420 |
|---|---|---|---|---|---|
| TCCAGTATTT | ATGACGGGGT | TCAAAGGCCT | CTGCACGTCC | TGCTTGAAAA | AATGGGTAGC |
| 430 | 440 | 450 | 460 | 470 | 480 |
| TTCATCCAGA | GAGGTGTCAG | CGCAGATGGG | CTTGATCATA | AGAAACTCTG | GGATTTCAAA |
| 490 | 500 | 510 | 520 | 530 | 540 |
| CCCATTGTCA | AGAAGGGCGA | TTCCGTAAAA | GGTGGAGACG | TAATTGGTGT | TGTACAGGAA |
| 550 | 560 | 570 | 580 | 590 | 600 |
| ACCGTGAATA | TTGAACATAA | GATCATGGTG | CCTCCTGATA | TCTCAGGTAC | AATTTCCGAC |
| 610 | 620 | 630 | 640 | 650 | 660 |
| ATAAAGAGCG | GAAACTTTAC | GGTAGTAGAC | ACAATCTGTA | CTCTGACTGA | TGGGACCGAA |
| 670 | 680 | 690 | 700 | 710 | 720 |
| TTGCAGATGA | TGCAGAGGTG | GCCTGTTCGA | AGACCCAGAC | CTGTGAAGGC | AAAACTTACT |
| 730 | 740 | 750 | 760 | 770 | 780 |
| CCAACCAGGC | CTCTGGTTAC | AGGAATGAGA | ATCCTTGATG | GGCTTTTCCC | TGTGGCAAAA |
| 790 | 800 | 810 | 820 | 830 | 840 |
| GGCGGAACAG | CTGCAATCCC | CGGACCTTTC | GGATCGGGAA | AGACCGTAAC | TCAGCAGTCG |
| 850 | 860 | 870 | 880 | 890 | 900 |
| CTTGCAAAAT | GGAGTGATAC | CGAAATTGTG | GTCTACATCG | GTTGTGGTGA | GCGTGGAAAC |
| 910 | 920 | 930 | 940 | 950 | 960 |
| GAAATGGCAG | ATGTTCTGAG | CGAATTCCCT | GAACTCGAAG | ATCCGCAGAC | CGGGCGCCCA |
| 970 | 980 | 990 | 1000 | 1010 | 1020 |
| CTTATGGAGC | GTACTGTTCT | TATCGCTAAC | ACTTCAAACA | TGCCTGTGGC | CGCAAGAGAA |
| 1030 | 1040 | 1050 | 1060 | 1070 | 1080 |
| GCATCTGTGT | ATACCGGAAT | CACCATTGCA | GAATACTACC | GTGACATGGG | ATTAGATGTA |
| 1090 | 1100 | 1110 | 1120 | 1130 | 1140 |
| TCCCTTATGG | CAGACTCCAC | CTCAAGGTGG | GCAGAAGCCA | TGAGAGAAAT | CTCTTCCCGT |
| 1150 | 1160 | 1170 | 1180 | 1190 | 1200 |
| CTGGAAGAAA | TGCCTGGTGA | AGAAGGTTAC | CCAGCATACC | TGTCTGCAAG | ACTGGCCGAA |
| 1210 | 1220 | 1230 | 1240 | 1250 | 1260 |
| TTCTACGAGC | GTGCCGGGGT | TGCGGAGAGT | CTTTGCGGCG | AAACAGGTTC | CATTACTGTT |
| 1270 | 1280 | 1290 | 1300 | 1310 | 1320 |
| ATTGGAGCAG | TATCTCCACC | TGGCGGTGAC | TTCTCAGAGC | CTGTTACACA | GAATACCCTG |
| 1330 | 1340 | 1350 | 1360 | 1370 | 1380 |
| CGTATCGTAA | AAGTGTTCTG | GGCTCTCGAT | GCCAAACTAT | CTCAGAGGCG | TCACTTCCCG |
| 1390 | 1400 | 1410 | 1420 | 1430 | 1440 |
| GCCATCAACT | GGCTGAACAG | TTACAGTCTG | TATAAGGACA | GTCTTAATGA | CTGGTTTGCA |
| 1450 | 1460 | 1470 | 1480 | 1490 | 1500 |
| GATAATGTGG | CTCCTGATTA | TGTGCCTTTG | AGGGAAAGAG | CAATGGAAAT | GCTCCAGACA |
| 1510 | 1520 | 1530 | 1540 | 1550 | 1560 |
| GAATCTGAAC | TGCAGGAAAT | CGTGCAGCTT | GTAGGTTCCG | ATGCTCTGCC | AGACGACCAG |
| 1570 | 1580 | 1590 | 1600 | 1610 | 1620 |
| CAGCTTCTGC | TTGAAATCAC | CCGTATGCTT | AGGGAAATTT | TCCTGCAGCA | GAATGCATTC |
| 1630 | 1640 | 1650 | 1660 | 1670 | 1680 |
| CACCCAGTAG | ATGCATACAG | CCCGTTCGAT | CAGCAGTACA | AGATCCTTAA | GGCAATCATG |
| 1690 | 1700 | 1710 | 1720 | 1730 | 1740 |
| AAATGGGGAG | ACGCTGCGAT | GGATGCCTTG | AAATCAGGTG | TTCCCGTAAC | TGAAATTATC |
| 1750 | 1760 | 1770 | 1780 | 1790 | 1800 |
| AAGCTTGAAT | CCAAAAATGT | GCTTGCTAAG | GTCAAGTACG | AAGAGAAGTT | TGATGAGTCT |
| 1810 | 1820 | 1830 | 1840 | 1850 | 1860 |
| ATGAATGCTG | TCCTGGCACA | GATGGATAAA | GAGTTTGCAT | CCCTGAGAGG | TAGGTAAATA |
| 1870 | 1880 | 1890 | 1900 | 1910 | 1920 |
| TGGTAAAAGA | GTATAAGACA | ATCACTCAGA | TTGCAGGACC | ACTTGTCTTT | GTTGAAAAAA |
| 1930 | 1940 | 1950 | 1960 | 1970 | 1980 |
| CAGAGCCTGT | AGGCTATAAA | GAAATTGTTA | CTATTAACTT | GCCTGACGGG | ACCACCCGCA |
| 1990 | 2000 | 2010 | 2020 | 2030 | 2040 |
| GAGGCGAGGT | GCTGGACTCA | TCTTCAGACA | TAGTGGTTAT | CCAGATTTTT | GAAGGTACTA |
| 2050 | 2060 | 2070 | 2080 | 2090 | 2100 |
| CTGGTCTGGA | CAAGGAATCG | GGTGTAGTCT | TTACAGGGGA | AACCCTGAAG | CTCCCTGCAT |
| 2110 | 2120 | 2130 | 2140 | 2150 | 2160 |
| CCATTGACCT | TCTCGGAAGA | ATCCTTTCAG | GTTCAGGAGA | ACCACTTGAC | GGTGGACCCA |
| 2170 | 2180 | 2190 | 2200 | 2210 | 2220 |
| GGATTGTGCC | CGACCAGCTT | CTGGACATCA | ACGGAGCTGC | AATGAACCCA | TATGCCAGGC |
| 2230 | 2240 | 2250 | 2260 | 2270 | 2280 |
| TGCCTCCAAA | GGATTTCATC | CAGACAGGTA | TCTCCACAAT | AGACGGAACA | AATACCCTTG |
| 2290 | 2300 | 2310 | 2320 | 2330 | 2340 |
| TCCGTGGACA | GAAACTGCCT | ATTTTCTCAG | CTTCAGGTCT | TCCACACAAC | GAAATTGCTC |
| 2350 | 2360 | 2370 | 2380 | 2390 | 2400 |
| TGCAGATCGC | AAGGCAGGCT | GCTGTGCCAG | GATCTGAATC | TGCTTTCGCA | GTAGTTTTTG |
| 2410 | 2420 | 2430 | 2440 | 2450 | 2460 |
| CAGCAATGGG | TATTACCAAT | GAAGAAGCCC | AGTACTTCAT | GAGCGACTTC | GAAAAGACCG |
| 2470 | 2480 | 2490 | 2500 | 2510 | 2520 |
| GGGCTCTTGA | AAGGGCTGTT | GTGTTCCTCA | ACCTTGCAGA | TGACCCTGCT | GTCGAACGTA |
| 2530 | 2540 | 2550 | 2560 | 2570 | 2580 |
| TAGTTACTCC | GCGTATGGCT | TTAACTGCAG | CTGAATATCT | GGCATACGAA | CACGGCATGC |
| 2590 | 2600 | 2610 | 2620 | 2630 | 2640 |
| ACGTACTTGT | CATTCTGACC | GACATTACCA | ACTATGCAGA | AGCTCTTCGT | CAGATGGGTG |
| 2650 | 2660 | 2670 | 2680 | 2690 | 2700 |
| CCGCTCGTAA | CGAAATCCCT | GGCCGTCGTG | GGTATCCTGG | TTACATGTAC | ACTGACCTTG |
| 2710 | 2720 | 2730 | 2740 | 2750 | 2760 |
| CAACTCTCTA | TGAGCGCGCA | GGTATTGTTA | AGGGCGCAAA | GGGATCAGTT | ACTCAGATTC |
| 2770 | 2780 | 2790 | 2800 | 2810 | 2820 |
| CGATTCTCTC | GATGCCTGGT | GACGATATTA | CCCACCCGAT | TCCTGACCTG | TCCGGTTATA |

| 2830 | 2840 | 2850 | 2860 | 2870 | 2880 |
|------|------|------|------|------|------|
| TTACTGAAGG | GCAGATTGTG | GTTTCAAGAG | AACTGCACAG | GAAAGGTATC | TACCCGCCAA |
| 2890 | 2900 | 2910 | 2920 | 2930 | 2940 |
| TTAATGTGTT | GCCGTCCCTG | TCAAGGTTGA | TGAACTCCGG | TATCGGAGCA | GGCAAGACAA |
| 2950 | 2960 | 2970 | 2980 | 2990 | 3000 |
| GAGAAGACCA | CAAGGCAGTT | TCTGACCAGA | TGTATGCAGG | TTATGCAGAA | GGGCGTGACC |
| 3010 | 3020 | 3030 | 3040 | 3050 | 3060 |
| TGAGAGGTCT | CGTGGCTATC | GTCGGTAAAG | AAGCTCTGTC | TGAGAGAGAC | GTCAAGTTCC |
| 3070 | 3080 | 3090 | 3100 | 3110 | 3120 |
| TTGAGTTTGC | TGACCTTTTC | GAACAGCAGT | TCGTTACACA | GGGCAGAAAC | GAAAACAGGA |
| 3130 | 3140 | 3150 | 3160 | 3170 | 3180 |
| CAATTGCAGA | CACTCTGGAC | ATTGGATGGA | AGATCCTTGC | ACACCTGCCT | GAAAACCAGC |
| 3190 | 3200 | 3210 | 3220 | 3230 | 3240 |
| TGGGTAGGAT | TGACAACAAA | TACATCCAGA | AATACCATCC | TGCACACAGA | AAGGGTCAGT |
| 3250 | 3260 | 3270 | 3280 | 3290 | 3300 |
| GATTACCATG | GCTCAAGACG | TAAAACCAAC | TCGGTCGGAG | CTGATTGAGC | TCAAGAAAAA |
| 3310 | 3320 | 3330 | 3340 | 3350 | 3360 |
| AATCAAGCTC | TCTGAAAGTG | GGCACAAGCT | CCTTAAGATG | AAGAGAGATG | GTCTTATTCT |

Of the above DNA sequences of the subunits, the 1st to 120th sequences are considered to be the sequence of these unidentified subunits of the ATP synthase, AGGTG at the 109th to 113th sequences, and AGG-TAG at the 1848th to 1853rd sequences are considered to be the SD sequences. The DNA which codes the α-subunit is found in the 121st to 1854th sequences, while the DNA which codes the β-subunit is found in the 1860th to 3239th sequences.

The amino acid sequence derived from the sequences of the thus determined α-subunit is as shown below. Incidentally, the starting codon GTG of the α-subunits is usually translated as valine, although in this subunit of the amino acid sequence, it was translated as methionine. Moreover, while the amino terminus of the β-subunit is shown to be methionine, the actual finding is that it started from barin (second codon) when the amino terminus of this β-subunit was subjected to the chemical assay. This is considered most probably to be the processing within the cell.

TABLE 2

| Amino acid | Three-letter abbreviation | One-letter symbol |
|------------|---------------------------|-------------------|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionite | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

| 10 | 20 | 30 | 40 | 50 | 60 |
|----|----|----|----|----|----|
| MEVKGEIYRV | SGPVVTAIGL | QAKMYDLVKV | GNEGLMGEVI | QILGPKTIIQ | VYEETAGIKP |
| 70 | 80 | 90 | 100 | 110 | 120 |
| GEPCVSTGSS | LSVELGPGLL | SSIYDGVQRP | LHVLLEKMGS | FIQRGVSADG | LDHKKLWDFK |
| 130 | 140 | 150 | 160 | 170 | 180 |
| PIVKKGDSVK | GGDVIGVVQE | TVNIEHKIMV | PPDISGTISD | IKSGNFTVVD | TICTLTDGTE |
| 190 | 200 | 210 | 220 | 230 | 240 |
| LQMMQRWPVR | RPRPVKAKLT | PTRPLVTGMR | ILDGLFPVAK | GGTAAIPGPF | GSGKTVTQQS |
| 250 | 260 | 270 | 280 | 290 | 300 |
| LAKWSDTEIV | VYIGCGERGN | EMADVLSEFP | ELEDPQTGRP | LMERTVLIAN | TSNMPVAARE |
| 310 | 320 | 330 | 340 | 350 | 360 |
| ASVYTGITIA | EYYRDMGLDV | SLMADSTSRW | AEAMREISSR | LEEMPGEEGY | PAYLSARLAE |
| 370 | 380 | 390 | 400 | 410 | 420 |
| FYERAGVAES | LCGETGSITV | IGAVSPPGGD | FSEPVTQNTL | RIVKVFWALD | AKLSQRRHFP |
| 430 | 440 | 450 | 460 | 470 | 480 |
| AINWLNSYSL | YKDSLNDWFA | DNVAPDYVPL | RERAMEMLQT | ESELQEIVQL | VGSDALPDDQ |
| 490 | 500 | 510 | 520 | 530 | 540 |
| QLLLEITRML | REIFLQQNAF | HPVDAYSPFD | QQYKILKAIM | KWGDAAMDAL | KSGVPVTEII |
| 550 | 560 | 570 | 580 | | |
| KLESKNVLAK | VKYEEKFDES | MNAVLAQMDK | EFASLRGR | | |

Various symbols in the above amino acid sequence respectively indicate those amino acids as shown in the following Table 2.

The amino acid sequence of the β-subunit determined in the same manner as above are shown below.

| 10 | 20 | 30 | 40 | 50 | 60 |
|----|----|----|----|----|----|
| VKEYKTITQI | AGPLVFVEKT | EPVGYKEIVT | INLPDGTTRR | GEVLDSSSDI | VVIQIFEGTT |
| 70 | 80 | 90 | 100 | 110 | 120 |
| GLDKECGVVF | TGETLKLPAS | IDLLGRILSG | SGEPLDGGPR | IVPDQLLDIN | GAAMNPYARL |
| 130 | | | | | |

-continued

| | | | | | |
|---|---|---|---|---|---|
| PPKDFIQTGI | STIDGTNTLV | RGQKLPIFSA | SGLPHNEIAL | QIARQAAVPG | SESAFAVVFA |
| 190 | 200 | 210 | 220 | 230 | 240 |
| AMGITNEEAQ | YFMSDFEKTG | ALERAVVFLN | LADDPAVERI | VTPRMALTAA | EYLAYEHGMH |
| 250 | 260 | 270 | 280 | 290 | 300 |
| VLVILTDITN | YAEALRQMGA | ARNEIPGRRG | YPGYMYTDLA | TLYERAGIVK | GAKGSVTQIP |
| 310 | 320 | 330 | 340 | 350 | 360 |
| ILSMPGDDIT | HPIPDLSGYI | TEGQIVVSRE | LHRKGIYPPI | NVLPSLSRLM | NSGIGAGKTR |
| 370 | 380 | 390 | 400 | 410 | 420 |
| EDHKAVSDQM | YAGYAEGRDL | RGLVAIVGKE | ALSERDVKFL | EFADLFEQQF | VTQGRNENRT |
| 430 | | 440 | 450 | 460 | |
| IADTLDIGWK | ILAHLPENQL | GRIDNKYIQK | YHPAHRKCQ | | |

By cloning DNA which codes the ATP synthase of the methanogenic bacteria and which determines the DNA sequence coding the α- and β-subunits, both being the main subunits of the ATP synthase, it is possible to manifest this gene within the methanogenic bacteria by carrying it with the plasmid and to improve the methanogenic bacteria. This DNA is also useful as a marker for plasmid used as a vector of the methanogenic bacteria.

What is claimed is:

1. A recombinant DNA sequence encoding at least one subunit of ATP synthase isolated from *Methanosarcina barkeri*, said subunit being selected from the group consisting of the α-subunit, the β-subunit and both the α-subunit and the β-subunit.

2. A DNA sequence according to claim 1, wherein, of the subunits of said ATP synthase, α-subunit is indicated by the following amino acid sequence

| | | | | | |
|---|---|---|---|---|---|
| 10 | 20 | 30 | 40 | 50 | 60 |
| MEVKGEIYRV | SGPVVTAIGL | QAKMYDLVKV | GNEGLMGEVI | QILGPKTIIQ | VYEETAGIKP |
| 70 | 80 | 90 | 100 | 110 | 120 |
| GEPCVSTGSS | LSVELGPGLL | SSIYDGVQRP | LHVLLEKMGS | FIQRGVSADG | LDHKKLWDFK |
| 130 | 140 | 150 | 160 | 170 | 180 |
| PIVKKGDSVK | GGDVIGVVQE | TVNIEHKIMV | PPDISGTISD | IKSGNFTVVD | TICTLTDGTE |
| 190 | 200 | 210 | 220 | 230 | 240 |
| LQMMQRWPVR | RPRPVKAKLT | PTRPLVTGMR | ILDGLFPVAK | GGTAAIPGPF | GSGKTVTQQS |
| 250 | 260 | 270 | 280 | 290 | 300 |
| LAKWSDTEIV | VYIGCGERGN | EMADVLSEFP | ELEDPQTGRP | LMERTVLIAN | TSNMPVAARE |
| 310 | 320 | 330 | 340 | 350 | 360 |
| ASVYTGITIA | EYYRDMGLDV | SLMADSTSRW | AEAMREISSR | LEEMPGEEGY | PAYLSARLAE |
| 370 | 380 | 390 | 400 | 410 | 420 |
| FYERAGVAES | LCGETGSITV | IGAVSPPGGD | FSEPVTQNTL | RIVKVFWALD | AKLSQRRHFP |
| 430 | 440 | 450 | · 460 | 470 | 480 |
| AINWLNSYSL | YKDSLNDWFA | DNVAPDYVPL | RERAMEMLQT | ESELQEIVQL | VGSDALPDDQ |
| 490 | 500 | 510 | 520 | 530 | 540 |
| QLLLEITRML | REIFLQQNAF | HPVDAYSPFD | QQYKILKAIM | KWGDAAMDAL | KSGVPVTEII |
| 550 | 560 | 570 | 580 | | |
| KLESKNVLAK | VKYEEKFDES | MNAVLAQMDK | EFASLRGR . | | |

3. A DNA sequence according to claim 1, wherein, of the subunits of said ATP synthase, β-subunit is indicated by the following amino acid sequence

| | | | | | |
|---|---|---|---|---|---|
| 10 | 20 | 30 | 40 | 50 | 60 |
| VKEYKTITQI | AGPLVFVEKT | EPVGYKEIVT | INLPDGTTRR | GEVLDSSSDI | VVIQIFEGTT |
| 70 | 80 | 90 | 100 | 110 | 120 |
| GLDKECGVVF | TGETLKLPAS | IDLLGRILSG | SGEPLDGGPR | IVPDQLLDIN | GAAMNPYARL |
| 130 | 140 | 150 | 160 | 170 | 180 |
| PPKDFIQTGI | STIDGTNTLV | RGQKLPIFSA | SGLPHNEIAL | QIARQAAVPG | SESAFAVVFA |
| 190 | 200 | 210 | 220 | 230 | 240 |
| AMGITNEEAQ | YFMSDFEKTG | ALERAVVFLN | LADDPAVERI | VTPRMALTAA | EYLAYEHGMH |
| 250 | 260 | 270 | 280 | 290 | 300 |
| VLVILTDITN | YAEALRQMGA | ARNEIPGRRG | YPGYMYTDLA | TLYERAGIVK | GAKGSVTQIP |
| 310 | 320 | 330 | 340 | 350 | 360 |
| ILSMPGDDIT | HPIPDLSGYI | TEGQIVVSRE | LHRKGIYPPI | NVLPSLSRLM | NSGIGAGKTR |
| 370 | 380 | 390 | 400 | 410 | 420 |
| EDHKAVSDQM | YAGYAEGRDL | RGLVAIVGKE | ALSERDVKFL | EFADLFEQQF | VTQGRNENRT |
| 430 | 440 | 450 | 460 | | |
| IADTLDIGWK | ILAHLPENQL | GRIDNKYIQK | YHPAHRKCQ. | | |

4. A DNA sequence according to claim 1, which contains the following sequences and encodes both the α- and β-subunits as the main subunits

| | | | | | |
|---|---|---|---|---|---|
| 10 | 20 | 30 | 40 | 50 | 60 |
| GCCGGAAATT | CTAAGGAAAA | ACTTGAATGA | GTCTGTCCAG | CCTACAGTAG | TAGCCCTGGG |
| 70 | 80 | 90 | 100 | 110 | 120 |
| AGGCAGTGGA | TCAGGCTCAA | ATCTAAGAGA | TAAGATAAAA | CAAGCGGTAG | GTGTTGATCT |
| 130 | 140 | 150 | 160 | 170 | 180 |
| GTGGAAGTAA | AAGGTGAAAT | TTATCGTGTG | TCTGGGCCTG | TCGTCACCGC | CATCGGCTTG |
| 190 | 200 | 210 | 220 | 230 | 240 |
| CAGGCAAAAA | TGTATGACCT | GGTCAAAGTC | GGTAATGAAG | GTTTAATGGG | TGAAGTCATT |
| 250 | 260 | 270 | 280 | 290 | 300 |
| CAGATATTAG | GGCCCAAGAC | CATCATCCAG | GTATATGAAG | AGACCGCAGG | TATCAAGCCA |

-continued

| 310 | 320 | 330 | 340 | 350 | 360 |
|---|---|---|---|---|---|
| GGGGAACCCT | GTGTATCTAC | AGGGTCGTCT | CTGTCCGTAG | AACTTGGTCC | GGGTCTTCTT |
| 370 | 380 | 390 | 400 | 410 | 420 |
| TCCAGTATTT | ATGACGGGGT | TCAAAGGCCT | CTGCACGTCC | TGCTTGAAAA | AATGGGTAGC |
| 430 | 440 | 450 | 460 | 470 | 480 |
| TTCATCCAGA | GAGGTGTCAG | CGCAGATGGG | CTTGATCATA | AGAAACTCTG | GGATTTCAAA |
| 490 | 500 | 510 | 520 | 530 | 540 |
| CCCATTGTCA | AGAAGGGCGA | TTCCGTAAAA | GGTGGAGACG | TAATTGGTGT | TGTACAGGAA |
| 550 | 560 | 570 | 580 | 590 | 600 |
| ACCGTGAATA | TTGAACATAA | GATCATGGTG | CCTCCTGATA | TCTCAGGTAC | AATTTCCGAC |
| 610 | 620 | 630 | 640 | 650 | 660 |
| ATAAAGAGCG | GAAACTTTAC | GGTAGTAGAC | ACAATCTGTA | CTCTGACTGA | TGGGACCGAA |
| 670 | 680 | 690 | 700 | 710 | 720 |
| TTGCAGATGA | TGCAGAGGTG | GCCTGTTCGA | AGACCCAGAC | CTGTGAAGGC | AAAACTTACT |
| 730 | 740 | 750 | 760 | 770 | 780 |
| CCAACCAGGC | CTCTGGTTAC | AGGAATGAGA | ATCCTTGATG | GGCTTTTCCC | TGTGGCAAAA |
| 790 | 800 | 810 | 820 | 830 | 840 |
| GGCGGAACAG | CTGCAATCCC | CGGACCTTTC | GGATCGGGAA | AGACCGTAAC | TCAGCAGTCG |
| 850 | 860 | 870 | 880 | 890 | 900 |
| CTTGCAAAAT | GGAGTGATAC | CGAAATTGTG | GTCTACATCG | GTTGTGGTGA | GCGTGGAAAC |
| 910 | 920 | 930 | 940 | 950 | 960 |
| GAAATGGCAG | ATGTTCTGAG | CGAATTCCCT | GAACTCGAAG | ATCCGCAGAC | CGGGCGCCCA |
| 970 | 980 | 990 | 1000 | 1010 | 1020 |
| CTTATGGAGC | GTACTGTTCT | TATCGCTAAC | ACTTCAAACA | TGCCTGTGGC | CGCAAGAGAA |
| 1030 | 1040 | 1050 | 1060 | 1070 | 1080 |
| GCATCTGTGT | ATACCGGAAT | CACCATTGCA | GAATACTACC | GTGACATGGG | ATTAGATGTA |
| 1090 | 1100 | 1110 | 1120 | 1130 | 1140 |
| TCCCTTATGG | CAGACTCCAC | CTCAAGGTGG | GCAGAAGCCA | TGAGAGAAAT | CTCTTCCCGT |
| 1150 | 1160 | 1170 | 1180 | 1190 | 1200 |
| CTGGAAGAAA | TGCCTGGTGA | AGAAGGTTAC | CCAGCATACC | TGTCTGCAAG | ACTGGCCGAA |
| 1210 | 1220 | 1230 | 1240 | 1250 | 1260 |
| TTCTACGAGC | GTGCCGGGGT | TGCGGAGAGT | CTTTGCGGCG | AAACAGGTTC | CATTACTGTT |
| 1270 | 1280 | 1290 | 1300 | 1310 | 1320 |
| ATTGGAGCAG | TATCTCCACC | TGGCGGTGAC | TTCTCAGAGC | CTGTTACACA | GAATACCCTG |
| 1330 | 1340 | 1350 | 1360 | 1370 | 1380 |
| CGTATCGTAA | AAGTGTTCTG | GGCTCTCGAT | GCCAAACTAT | CTCAGAGGCG | TCACTTCCCG |
| 1390 | 1400 | 1410 | 1420 | 1430 | 1440 |
| GCCATCAACT | GGCTGAACAG | TTACAGTCTG | TATAAGGACA | GTCTTAATGA | CTGGTTTGCA |
| 1450 | 1460 | 1470 | 1480 | 1490 | 1500 |
| GATAATGTGG | CTCCTGATTA | TGTGCCTTTG | AGGGAAAGAG | CAATGGAAAT | GCTCCAGACA |
| 1510 | 1520 | 1530 | 1540 | 1550 | 1560 |
| GAATCTGAAC | TGCAGGAAAT | CGTGCAGCTT | GTAGGTTCCG | ATGCTCTGCC | AGACGACCAG |
| 1570 | 1580 | 1590 | 1600 | 1610 | 1620 |
| CAGCTTCTGC | TTGAAATCAC | CCGTATGCTT | AGGGAAATTT | TCCTGCAGCA | GAATGCATTC |
| 1630 | 1640 | 1650 | 1660 | 1670 | 1680 |
| CACCCAGTAG | ATGCATACAG | CCCGTTCGAT | CAGCAGTACA | AGATCCTTAA | GGCAATCATG |
| 1690 | 1700 | 1710 | 1720 | 1730 | 1740 |
| AAATGGGGAG | ACGCTGCGAT | GGATGCCTTG | AAATCAGGTG | TTCCCGTAAC | TGAAATTATC |
| 1750 | 1760 | 1770 | 1780 | 1790 | 1800 |
| AAGCTTGAAT | CCAAAAATGT | GCTTGCTAAG | GTCAAGTACG | AAGAGAAGTT | TGATGAGTCT |
| 1810 | 1820 | 1830 | 1840 | 1850 | 1860 |
| ATGAATGCTG | TCCTGGCACA | GATGGATAAA | GAGTTTGCAT | CCCTGAGAGG | TAGGTAAATA |
| 1870 | 1880 | 1890 | 1900 | 1910 | 1920 |
| TGGTAAAAGA | GTATAAGACA | ATCACTCAGA | TTGCAGGACC | ACTTGTCTTT | GTTGAAAAAA |
| 1930 | 1940 | 1950 | 1960 | 1970 | 1980 |
| CAGAGCCTGT | AGGCTATAAA | GAAATTGTTA | CTATTAACTT | GCCTGACGGG | ACCACCCGCA |
| 1990 | 2000 | 2010 | 2020 | 2030 | 2040 |
| GAGGCGAGGT | GCTGGACTCA | TCTTCAGACA | TAGTGGTTAT | CCAGATTTTT | GAAGGTACTA |
| 2050 | 2060 | 2070 | 2080 | 2090 | 2100 |
| CTGGTCTGGA | CAAGGAATCG | GGTGTAGTCT | TTACAGGGGA | AACCCTGAAG | CTCCCTGCAT |
| 2110 | 2120 | 2130 | 2140 | 2150 | 2160 |
| CCATTGACCT | TCTCGGAAGA | ATCCTTTCAG | GTTCAGGAGA | ACCACTTGAC | GGTGGACCCA |
| 2170 | 2180 | 2190 | 2200 | 2210 | 2220 |
| GGATTGTGCC | CGACCAGCTT | CTGGACATCA | ACGGAGCTGC | AATGAACCCA | TATGCCAGGC |
| 2230 | 2240 | 2250 | 2260 | 2270 | 2280 |
| TGCCTCCAAA | GGATTTCATC | CAGACAGGTA | TCTCCACAAT | AGACGGAACA | AATACCCTTG |
| 2290 | 2300 | 2310 | 2320 | 2330 | 2340 |
| TCCGTGGACA | GAAACTGCCT | ATTTTCTCAG | CTTCAGGTCT | TCCACACAAC | GAAATTGCTC |
| 2350 | 2360 | 2370 | 2380 | 2390 | 2400 |
| TGCAGATCGC | AAGGCAGGCT | GCTGTGCCAG | GATCTGAATC | TGCTTTCGCA | GTAGTTTTTG |
| 2410 | 2420 | 2430 | 2440 | 2450 | 2460 |
| CAGCAATGGG | TATTACCAAT | GAAGAAGCCC | AGTACTTCAT | GAGCGACTTC | GAAAAGACCG |
| 2470 | 2480 | 2490 | 2500 | 2510 | 2520 |
| GGGCTCTTGA | AAGGGCTGTT | GTGTTCCTCA | ACCTTGCAGA | TGACCCTGCT | GTCGAACGTA |
| 2530 | 2540 | 2550 | 2560 | 2570 | 2580 |
| TAGTTACTCC | GCGTATGGCT | TTAACTGCAG | CTGAATATCT | GGCATACGAA | CACGGCATGC |
| 2590 | 2600 | 2610 | 2620 | 2630 | 2640 |
| ACGTACTTGT | CATTCTGACC | GACATTACCA | ACTATGCAGA | AGCTCTTCGT | CAGATGGGTG |
| 2650 | 2660 | 2670 | 2680 | 2690 | 2700 |
| CCGCTCGTAA | CGAAATCCCT | GGCCGTCGTG | GGTATCCTGG | TTACATGTAC | ACTGACCTTG |
| 2710 | 2720 | 2730 | 2740 | 2750 | 2760 |
| CAACTCTCTA | TGAGCGCGCA | GGTATTGTTA | AGGGCGCAAA | GGGATCAGTT | ACTCAGATTC |

-continued

| 2770 | 2780 | 2790 | 2800 | 2810 | 2820 |
|---|---|---|---|---|---|
| CGATTCTCTC | GATGCCTGGT | GACGATATTA | CCCACCCGAT | TCCTGACCTG | TCCGGTTATA |
| 2830 | 2840 | 2850 | 2860 | 2870 | 2880 |
| TTACTGAAGG | GCAGATTGTG | GTTTCAAGAG | AACTGCACAG | GAAAGGTATC | TACCCGCCAA |
| 2890 | 2900 | 2910 | 2920 | 2930 | 2940 |
| TTAATGTGTT | GCCGTCCCTG | TCAAGGTTGA | TGAACTCCGG | TATCGGAGCA | GGCAAGACAA |
| 2950 | 2960 | 2970 | 2980 | 2990 | 3000 |
| GAGAAGACCA | CAAGGCAGTT | TCTGACCAGA | TGTATGCAGG | TTATGCAGAA | GGGCGTGACC |
| 3010 | 3020 | 3030 | 3040 | 3050 | 3060 |
| TGAGAGGTCT | CGTGGCTATC | GTCGGTAAAG | AAGCTCTGTC | TGAGAGAGAC | GTCAAGTTCC |
| 3070 | 3080 | 3090 | 3100 | 3110 | 3120 |
| TTGAGTTTGC | TGACCTTTTC | GAACAGCAGT | TCGTTACACA | GGGCAGAAAC | GAAAACAGGA |
| 3130 | 3140 | 3150 | 3160 | 3170 | 3180 |
| CAATTGCAGA | CACTCTGGAC | ATTGGATGGA | AGATCCTTGC | ACACCTGCCT | GAAAACCAGC |
| 3190 | 3200 | 3210 | 3220 | 3230 | 3240 |
| TGGGTAGGAT | TGACAACAAA | TACATCCAGA | AATACCATCC | TGCACACAGA | AAGGGTCAGT |
| 3250 | 3260 | 3270 | 3280 | 3290 | 3300 |
| GATTACCATG | GCTCAAGACG | TAAAACCAAC | TCGGTCGGAG | CTGATTGAGC | TCAAGAAAAA |
| 3310 | 3320 | 3330 | 3340 | 3350 | 3360 |
| AATCAAGCTC | TCTGAAAGTG | GGCACAAGCT | CCTTAAGATG | AAGAGAGATG | GTCTTATTCT. |